(12) United States Patent
Limanskiy

(10) Patent No.: US 12,181,200 B2
(45) Date of Patent: Dec. 31, 2024

(54) REFRIGERATOR SYSTEM

(71) Applicant: WHIRLPOOL CORPORATION, Benton Harbor, MI (US)

(72) Inventor: Semen Viktorovich Limanskiy, Lipetsk (RU)

(73) Assignee: Whirlpool Corporation, Benton Harbor, MI (US)

( * ) Notice: Subject to any disclaimer, the term of this patent is extended or adjusted under 35 U.S.C. 154(b) by 272 days.

(21) Appl. No.: 17/748,599

(22) Filed: May 19, 2022

(65) Prior Publication Data

US 2022/0275991 A1     Sep. 1, 2022

Related U.S. Application Data

(62) Division of application No. 17/120,915, filed on Dec. 14, 2020, now Pat. No. 11,384,974.

(51) Int. Cl.
*F25D 17/04* (2006.01)
*F25D 27/00* (2006.01)

(52) U.S. Cl.
CPC .......... *F25D 17/042* (2013.01); *F25D 27/00* (2013.01); *F25D 2317/0416* (2013.01); *F25D 2317/0417* (2013.01); *F25D 2400/22* (2013.01)

(58) Field of Classification Search
CPC .......... F25D 2317/04; F25D 2317/041; F25D 2317/0413; F25D 2317/04131; F25D 2317/0416; F25D 2317/0417; F25D 2327/00; F25D 2400/22; F25D 17/00; F25D 17/02; F25D 17/005; F25D 17/04; F25D 17/042; F25D 23/065; F25D 23/067; F25D 27/00; F25D 27/005; F25D 2317/063; F25D 2317/067; F25D 2317/0672; F25D 23/06; F25D 23/061; F25D 23/063; F25D 23/066
See application file for complete search history.

(56) References Cited

U.S. PATENT DOCUMENTS

| | | | |
|---|---|---|---|
| 3,933,398 A * | 1/1976 | Haag | F25D 23/067 62/DIG. 13 |
| 4,752,171 A * | 6/1988 | Pliml, Jr. | B29C 65/069 411/181 |
| 4,955,208 A | 9/1990 | Kawashima et al. | |
| 5,230,220 A | 7/1993 | Kang et al. | |

(Continued)

FOREIGN PATENT DOCUMENTS

| | | |
|---|---|---|
| AU | 2018102157 A4 | 3/2020 |
| CN | 2401534 Y | 10/2000 |

(Continued)

*Primary Examiner* — Andrew Roersma
(74) *Attorney, Agent, or Firm* — Brooks Kushman P.C.

(57) ABSTRACT

A fixation system for use in a refrigerator, including an insulative member and a ventilation panel defining a number of vents, includes first and second straps. The second strap is spaced apart from the first strap. The first strap and the second strap are collectively configured to receive the insulative member. The first strap includes a main body having a rear side and a front side opposing the rear side. The rear side is configured to lie against a rear wall of the refrigerator and defines a first aperture configured to receive a first fastener to fix the main body to the rear wall of the refrigerator. The front side defines a second aperture configured to receive a second fastener to fix the ventilation panel to the main body.

14 Claims, 8 Drawing Sheets

(56) References Cited

U.S. PATENT DOCUMENTS

| | | |
|---|---|---|
| 6,967,008 B1 | 11/2005 | Barnes |
| 7,107,785 B2 * | 9/2006 | Barmann ................ F25D 25/02 62/407 |
| 10,139,150 B2 | 11/2018 | De Cavalcanti et al. |
| 11,384,974 B2 * | 7/2022 | Limanskiy .............. F25D 27/00 |
| 2012/0036879 A1 | 2/2012 | Candeo et al. |
| 2018/0164021 A1 * | 6/2018 | Lindel .................... F25D 23/06 |
| 2018/0164029 A1 * | 6/2018 | Lindel ................ F25D 23/067 |
| 2018/0274850 A1 * | 9/2018 | Staud .................... F25D 23/066 |
| 2019/0249918 A1 * | 8/2019 | Marinello .............. F25D 23/02 |
| 2020/0124339 A1 | 4/2020 | Cheng et al. |

FOREIGN PATENT DOCUMENTS

| | | | |
|---|---|---|---|
| CN | 102365514 B | 4/2015 | |
| CN | 205641742 U | 10/2016 | |
| CN | 107036369 A | 8/2017 | |
| CN | 107218759 A * | 9/2017 | ............. F25D 11/02 |
| CN | 107782041 A * | 3/2018 | ........... F25D 17/062 |
| CN | 110895072 A | 3/2020 | |
| CN | 211214574 U | 8/2020 | |
| EP | 0282301 A1 | 9/1988 | |
| EP | 2401563 B1 | 10/2016 | |
| EP | 3343155 A1 | 7/2018 | |
| EP | 3608612 A1 * | 2/2020 | ........... F25D 17/062 |
| EP | 3643997 A1 | 4/2020 | |
| ES | 2073960 A2 | 8/1995 | |
| JP | S6449874 A | 2/1989 | |
| JP | H01266483 A | 10/1989 | |
| JP | H03101810 A | 4/1991 | |
| JP | H04306478 A | 10/1992 | |
| JP | 3338218 B2 | 10/2002 | |
| JP | 2002295948 A * | 10/2002 | |
| JP | 2003075046 A * | 3/2003 | |
| JP | 2005106298 A | 4/2005 | |
| JP | 2020524252 A | 8/2020 | |
| KR | 890008636 Y | 6/1986 | |
| KR | 20120007500 A | 1/2012 | |
| KR | 101923458 B1 | 11/2018 | |
| KR | 20190028037 A | 3/2019 | |
| WO | WO-2007031422 A2 * | 3/2007 | ........... F25D 17/062 |
| WO | 2010099464 A2 | 9/2010 | |
| WO | 2010099464 A3 | 9/2010 | |
| WO | 2018233479 A1 | 12/2018 | |

* cited by examiner

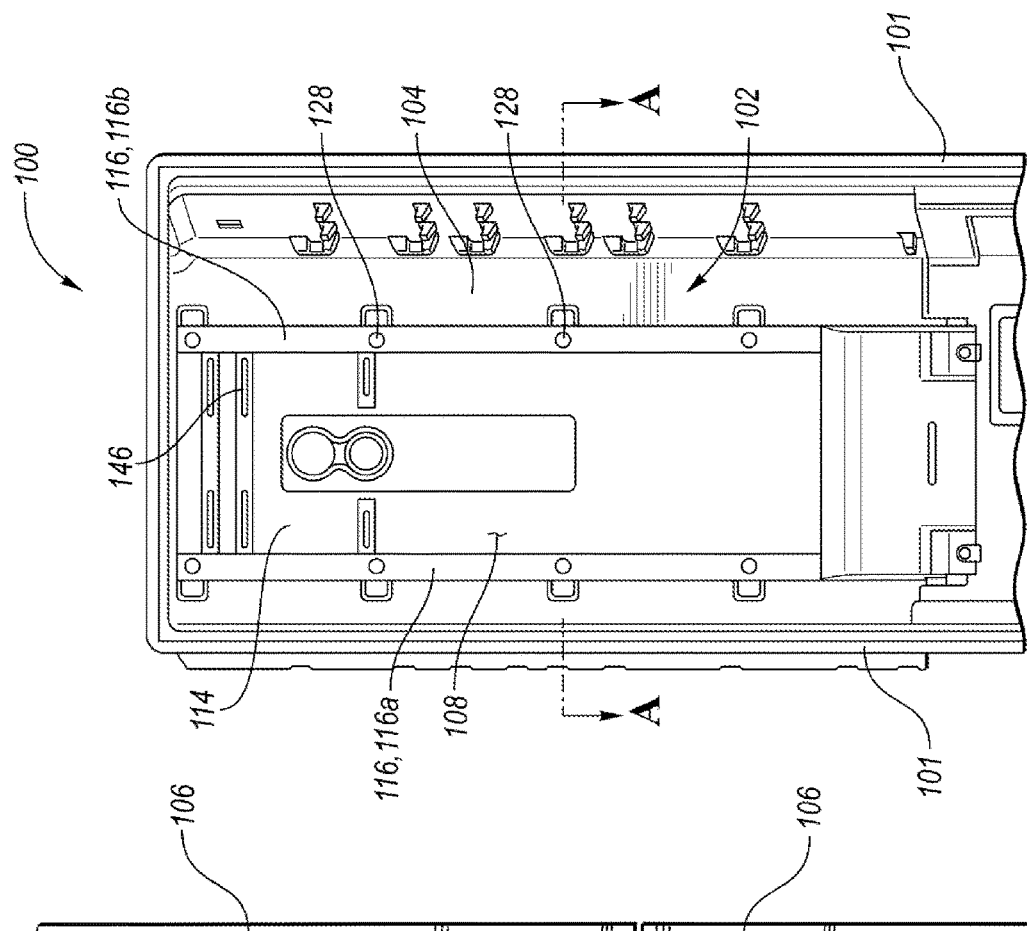
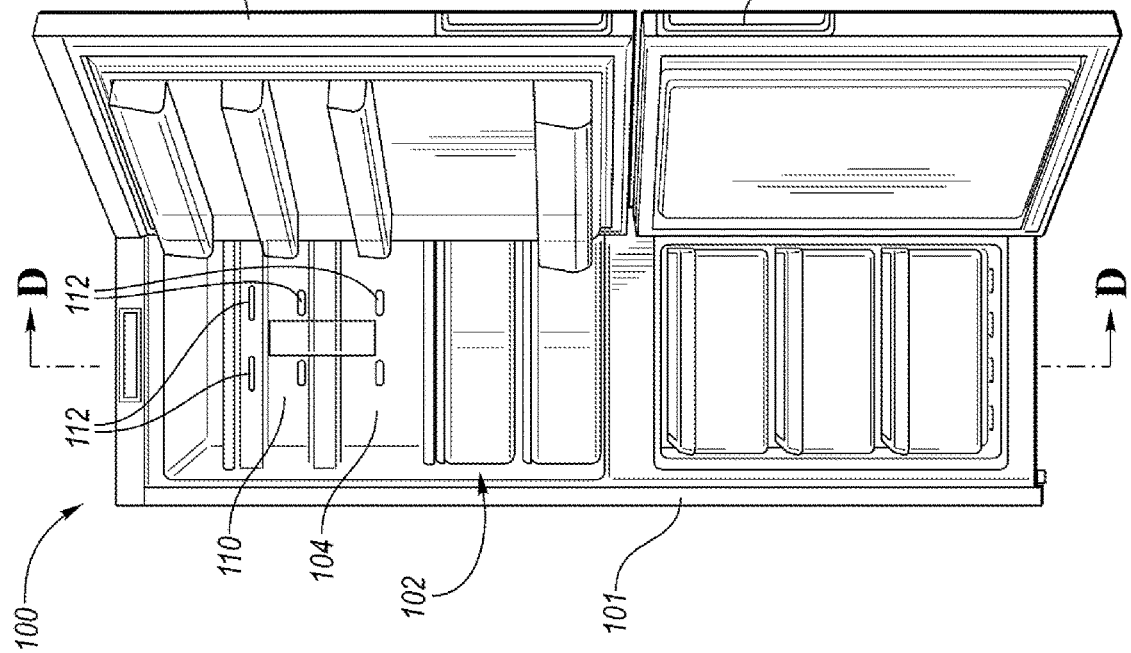

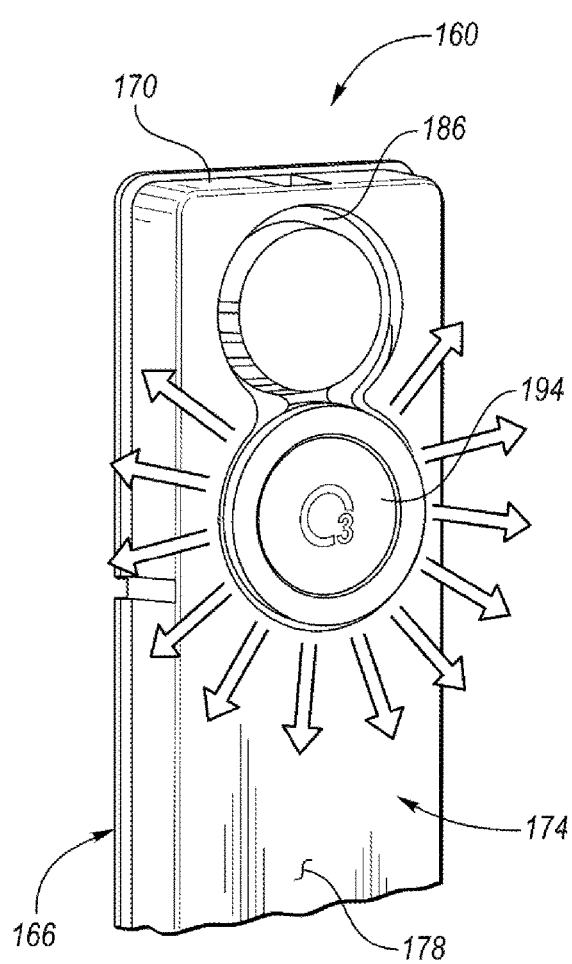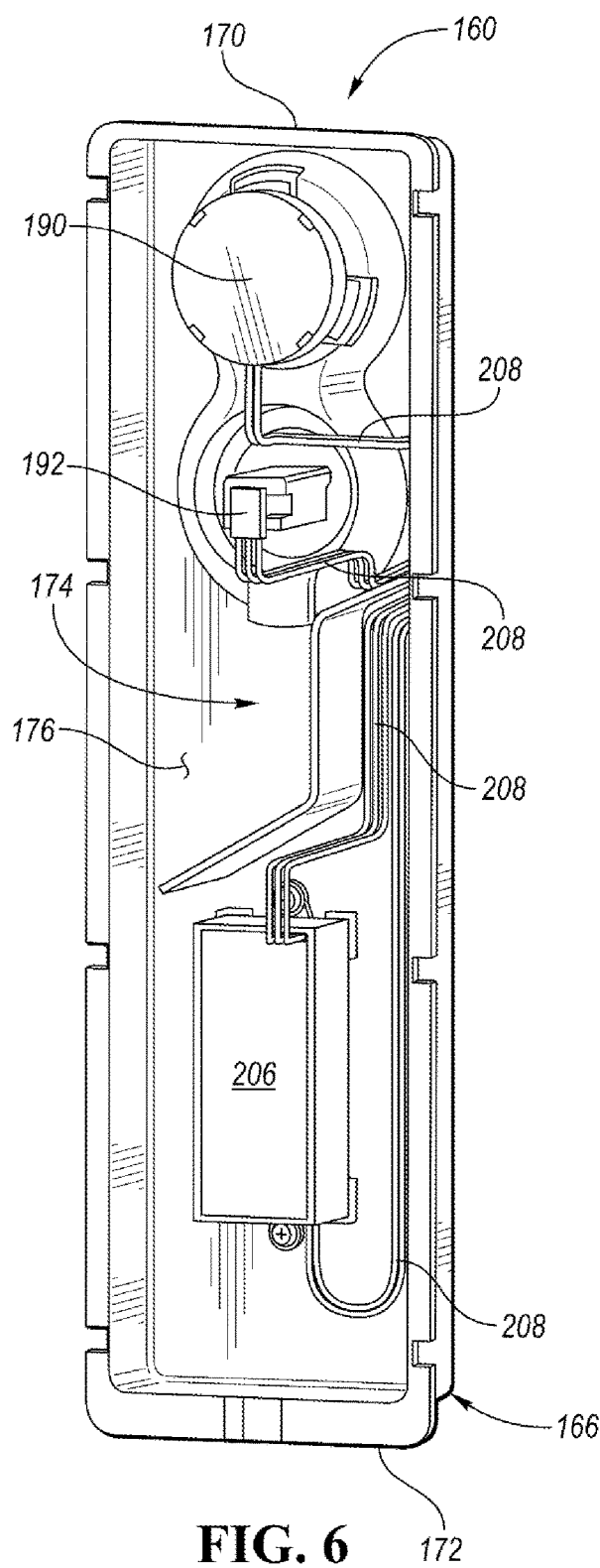
FIG. 5
FIG. 6

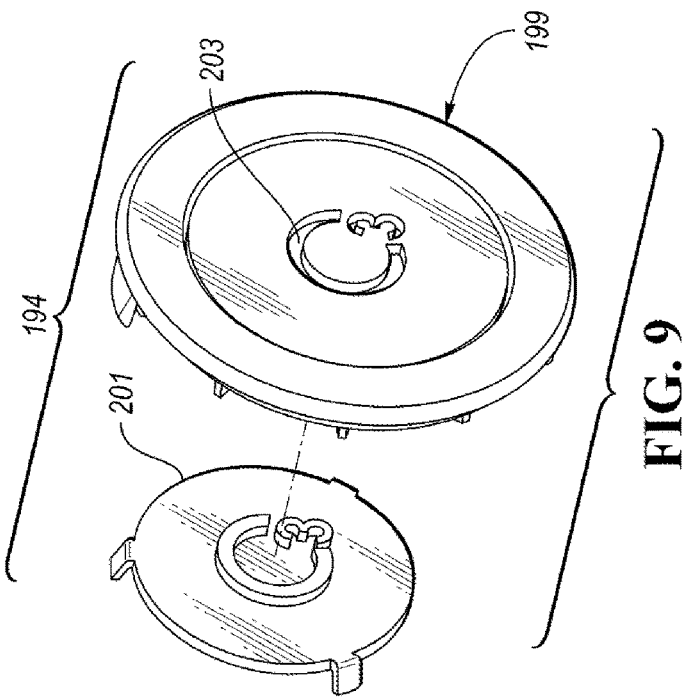
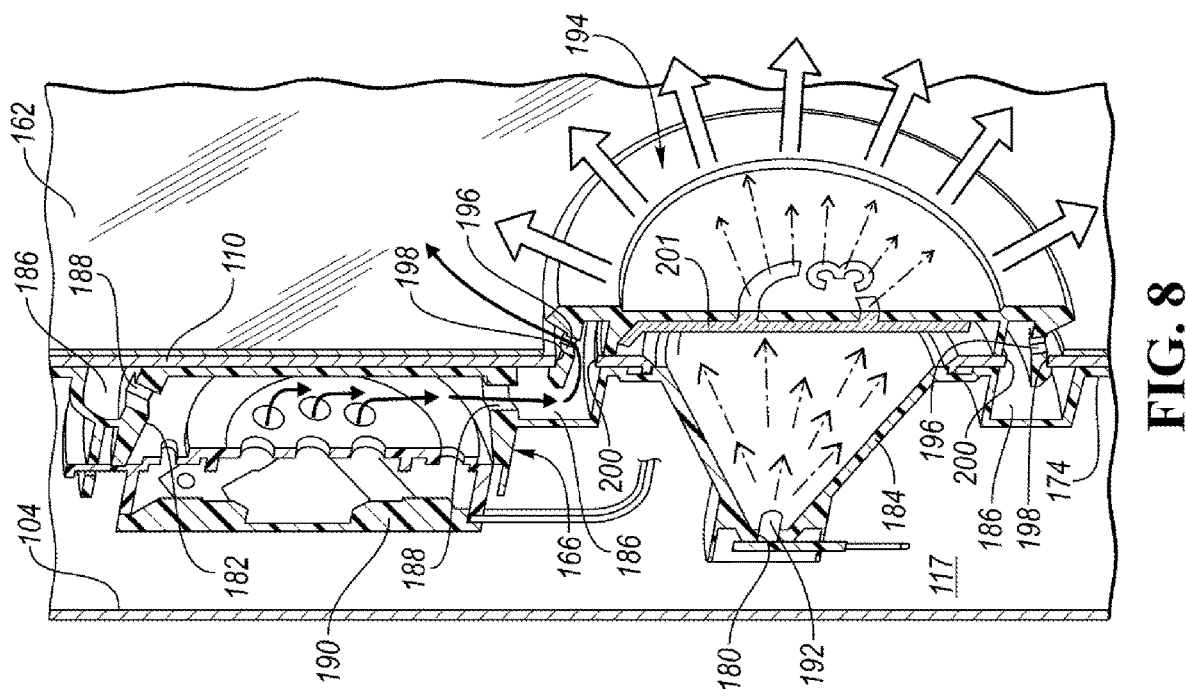

REFRIGERATOR SYSTEM

CROSS-REFERENCE TO RELATED APPLICATIONS

This application is a division of U.S. patent application Ser. No. 17/120,915 filed on Dec. 14, 2020, now U.S. Pat. No. 11,384,974, issued on Jul. 12, 2022, the disclosure of which is hereby incorporated in its entirety by reference herein.

TECHNICAL FIELD

The present disclosure relates to an appliance such as a refrigerator.

BACKGROUND

In order to keep food fresh, a low temperature must be maintained within a refrigerator to reduce the reproduction rate of harmful bacteria. Refrigerators circulate refrigerant and change the refrigerant from a liquid state to a gas state by an evaporation process. A compressor increases the pressure, and in turn, the temperature of the gas refrigerant. This heated gas is then cooled by ambient air received from one or more vents often disposed on a rear portion of the refrigerator.

SUMMARY

A fixation system for use in a refrigerator, including an insulative member and a ventilation panel defining a number of vents, includes first and second straps. The second strap is spaced apart from the first strap. The first strap and the second strap are collectively configured to receive the insulative member. The first strap includes a main body having a rear side and a front side opposing the rear side. The rear side is configured to lie against a rear wall of the refrigerator and defines a first aperture configured to receive a first fastener to fix the main body to the rear wall of the refrigerator. The front side defines a second aperture configured to receive a second fastener to fix the ventilation panel to the main body.

A refrigerator subcomponent fixation system includes a rear wall, an insulative member, a first strap, and a second strap. The first strap and the second strap are each fixed to the rear wall. The first strap and the second strap engage opposing sides of the insulative member to secure the insulative member to the rear wall.

A refrigerator subcomponent mounting system includes a rear wall, a ventilation panel, an insulative member, and at least one strap. The ventilation panel is spaced apart from the rear wall. The insulative member is disposed between the rear wall and the ventilation panel. The at least one strap is disposed between the rear wall and the ventilation panel. The at least one strap is fixed to the rear wall. The at least one strap engages the insulative member to secure the insulative member to the rear wall.

BRIEF DESCRIPTION OF THE DRAWINGS

FIG. 1 is a front view of an exemplary refrigerator;
FIG. 2 is a front view of a portion of the refrigerator with the shelving and storage bins removed;
FIG. 5 is a partial isometric front view of an ozone generator assembly;
FIG. 6 is an isometric rear view of the ozone generator assembly;
FIG. 8 is a partial isometric cross-sectional view taken along line D-D in FIG. 1;
and
FIG. 9 is an exploded isometric view of a light cover for the ozone generator assembly.

DETAILED DESCRIPTION

Figure 2A:
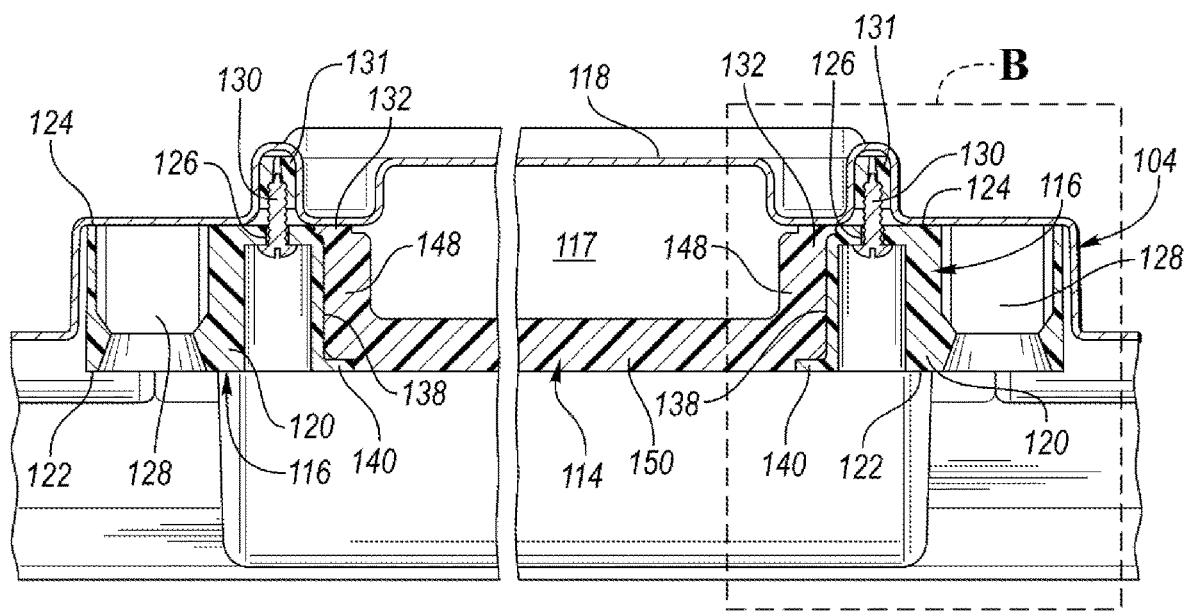
FIG. 2A is a partial cross-sectional view taken along line A-A in FIG. 2.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As used in the specification and the appended claims, the singular form "a," "an," and "the" comprise plural referents unless the context clearly indicates otherwise. For example, reference to a component in the singular is intended to comprise a plurality of components.

The term "substantially" or "about" may be used herein to describe disclosed or claimed embodiments. The term "substantially" or "about" may modify a value or relative characteristic disclosed or claimed in the present disclosure. In such instances, "substantially" or "about" may signify that the value or relative characteristic it modifies is within ±0%, 0.1%, 0.5%, 1%, 2%, 3%, 4%, 5% or 10% of the value or relative characteristic.

Spatially relative terms, such as "inner," "outer," "beneath," "below," "lower," "above," "upper," and the like, may be used for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Although the terms first, second, third, etc. may be used to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Refrigerators heat refrigerant by a compressor and then cool the refrigerant in a condenser, that may be mounted to a rear wall of the refrigerator. The rear wall of the refrigerator may include a number of vents that may draw in ambient air to cool the condenser and refrigerant contained therein. The rear wall within the refrigerator may include a ventilation panel that defines a number of vents configured to vent air from the interior of the refrigerator to the exterior of the refrigerator. Generally, the ventilation panel may be attached to an interior surface of the rear wall of the refrigerator by a number of fasteners such as screws. Fastening the panel by threading each of the screws may be time intensive. Moreover, the fasteners must be covered by a plug or cover to conceal the fastener and provide a more aesthetic appearance.

An insulative member may be disposed between the ventilation panel and the rear wall of the refrigerator. The insulative member may be inserted into a cavity or recessed portion defined by the rear wall of the refrigerator. As an example, the insulative member may be manually assembled to the rear wall by an operator. The operator subsequently fastens the ventilation panel to the rear wall of the refrigerator. In other words, the ventilation panel retains the insulative member between the ventilation panel and the rear wall. Because the insulative member is not directly fixed to the rear wall of the refrigerator, there may be gaps between the insulative member and the rear wall of the refrigerator. These gaps may lead to thermal inefficiencies.

Referring generally to the Figures, a refrigerator 100 according to one or more embodiments is provided. The refrigerator 100 may include several outer walls 101 that define an internal chamber 102. One of the outer walls may be a rear wall 104. One or more doors 106 may be pivotally attached to one of the outer walls 101. The rear wall 104 may include an interior surface 108 that is visible when one or more of the doors 106 is open. A ventilation panel 110 or flow panel may be disposed on the interior surface 108 of the rear wall 104. The ventilation panel 110 may include a number of apertures such as slots or vents 112 that may be configured to vent air (or facilitate an exchange of air) from the internal chamber 102 to an exterior of the refrigerator 100.

An insulative member 114 and a number of straps 116 may lie against a recessed portion 118 of the rear wall 104. As an example, the insulative member 114 may extend between a first strap 116a and a second strap 116b that may each be disposed within the recessed portion 118 of the rear wall 104. The ventilation panel 110 may be fixed to one or more of the straps 116 so that the insulative member 114 and straps 116 are sandwiched between the rear wall 104 and the ventilation panel 110. The insulative member 114 and the rear wall 104 may operate to form a duct 117 along a rear portion of the refrigerator (e.g., rear wall 104) to channel air from the internal chamber 102 to an exterior of the refrigerator 100. The slots or vents 112 of the ventilation panel 110 may be configured to vent air from the internal chamber 102 to the exterior of the refrigerator 100 via the duct 117.

In one or more embodiments, the insulative member 114 may be fixed to the first strap 116a and the second strap 116b by a press-fit condition. Alternatively, the insulative member 114 may be adhered to the straps 116 by an adhesive. As another example, one or more fasteners (not illustrated) may fix the insulative member 114 to the straps 116.

One or more of the straps 116 include a main body 120 provided with a rear side 124 and a front side 122 that opposes or is opposite to the rear side 124. In one or more embodiments, a sidewall 138 may extend between the rear side 124 and the front side 122. A flange 140 may extend from the sidewall 138 and engage portions of the insulative member 114.

The rear side 124 may define one or more first apertures 126 that each may be configured to receive a first fastener 130. The first fastener 130 may comprise one or more first fasteners 130. The one or more first apertures 126 each may be a portion of counterbore hole or may refer to a counterbore hole as a whole. The one or more first fasteners 130 may be configured to fix the straps 116 (or more specifically the main bodies 120 of the straps 116) to the rear wall 104. As an example, the one or more first fasteners 130 may be screws that are configured to thread into the rear wall 104 (or a more specifically into plugs 131 that are secured within recesses in the rear wall 104) to clamp the straps 116 and the insulative member 114 against the rear wall 104. In other words, the one or more first fasteners 130 may bias the strap 116 and insulative member 114 towards the rear wall 104 so that portions of the insulative member 114, such as protrusions 132, lie against the rear wall 104. The protrusions 132 may be configured to compress or deform as the first fastener 130 is tightened.

The front side 122 of the strap 116 may define one or more second apertures 128 that each may be configured to receive a second fastener 134. The second fastener 134 may comprise one or more second fasteners 134. The one or more second fasteners 134 may be configured to secure or fix the ventilation panel 110 to the straps 116. The one or more second apertures 128 each may be a portion of countersunk hole or may refer to a countersunk hole as a whole. The one or more second fasteners 134 may be a press-fit fasteners, such that pressing the one or more second fasteners 134 into the one or more second apertures 128 fixes the second fastener 134 and the ventilation panel 110 to the straps 116. For example, the one or more second apertures 128 may each include a first portion 142 and a second portion 144. The second portion 144 may extend from the front side 122 of the strap 116 and terminate at the first portion 142. The first portion 142 may extend from the rear side 124 of the strap and may have a substantially constant inner diameter. The second portion 144 may be tapered so that the one or more second fasteners 134 is retained within the second aperture 128 after insertion. Each of the one or more first apertures 126 may spaced apart from a respective sidewall 138 by a first width $W_1$ and each of the one or more second apertures 128 may be spaced apart from a respective sidewall 138 by a second width $W_2$ that is greater than the first width $W_1$.

The first width $W_1$ and the second width $W_2$ are illustrated as being measured to the center lines of the one or more first apertures 126 and the one or more second apertures 128. However, it should be understood the widths may be measured from any position within each aperture. For example, the widths may be measured from the closest or farthest edges of the respective apertures to the respective sidewall 138.

To install the insulative member 114 and the ventilation panel 110 to the rear wall 104 of the refrigerator, the insulative member 114 may be inserted between the first strap 116a and the second strap 116b such that the insulative member 114 is fixed therebetween. The first and second straps 116a, 116b may be fixed (e.g., fastened to the rear wall 104) such that the straps 116 and the insulative member 114 lie against the rear wall 104. The ventilation panel 110 may be pressed towards the strap 116 and the insulative member 114 so that the ventilation panel 110 is fixed to the strap 116.

FIG. 1 illustrates a front view of the refrigerator 100 in an assembled state. The ventilation panel 110 lies along portions of the rear wall 104 and covers the strap 116 and insulative member 114. The refrigerator 100 illustrated includes an upper refrigerator section and a lower freezer section. The refrigerator 100 illustrated also includes shelving and storage bins. However, the present disclosure applies to other configurations of refrigerators.

FIG. 2 illustrates a portion of the refrigerator 100 with the shelving, storage bins, and the ventilation panel 110 removed. The insulative member 114 may be elongated having a length that is greater than the width and may be disposed in the recessed portion 118 of the rear wall 104. As an example, the insulative member 114 may be formed of a cellular foam material such as a closed cell foam (e.g., expanded polystyrene). One or more apertures may form vents 146 in the insulative member 114 and the vents 146 may be substantially aligned with the vents 112 of the ventilation panel 110.

FIG. 2A illustrates a cross-sectional view of the insulative member 114, straps 116, and rear wall 104 taken along the line A-A in FIG. 2. The insulative member 114 may have a substantially U-shaped cross section including two legs 148 extending from a medial portion 150. The medial portion 150 and portions of the recessed portion 118 of the rear wall 104 may define the duct 117.

Figure 2B:
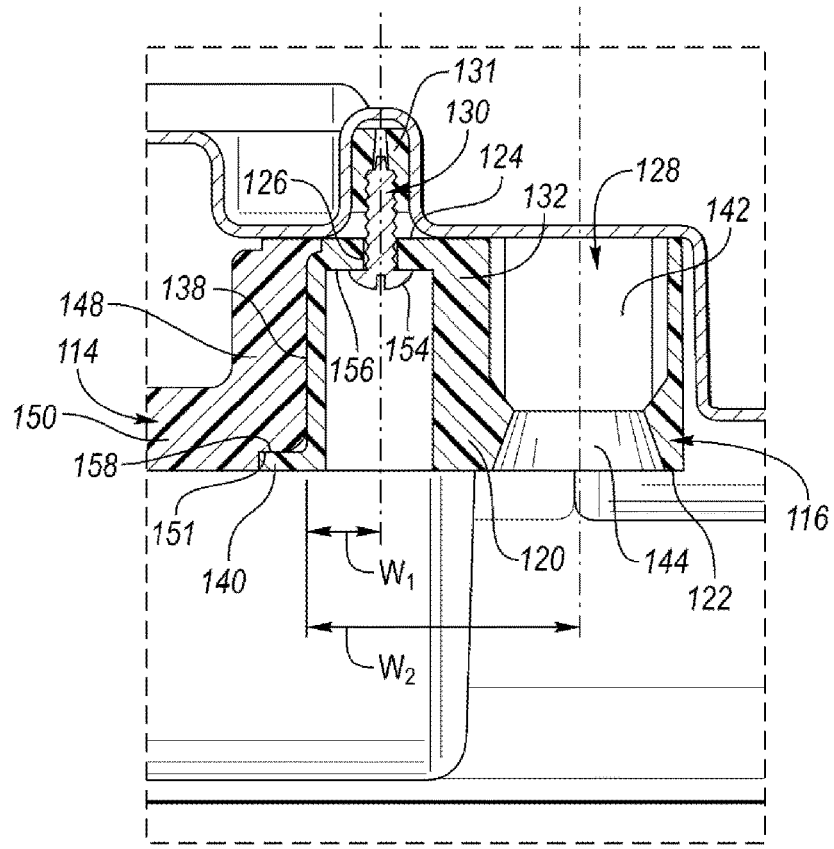
FIG. 2B is a magnified view of the area B in FIG. 2A.

FIG. 2B illustrates a detailed view of a portion of the insulative member 114, strap 116, and rear wall 104 encompassing the area B from FIG. 2A. Each of the legs 148 of the insulative member 114 and the medial portion 150 may define a recess portion 151 that may lie against the flange 140 of one of the straps 116 such that each strap 116 and the rear wall 104 sandwich one of the legs 148 of the insulative member 114. When the ventilation panel 110 is assembled to the straps 116, the flanges 140 may be sandwiched between the insulative member 114 (or more specifically the leg 148 of the insulative member 114) and the ventilation panel 110.

Each first fastener 130 may include a head 154 that may engage a clamping surface 156 on a respective strap 116. As the first fastener 130 is tightened, the flange 140 may engage and bias or clamp the leg 148 towards the rear wall 104. More specifically a clamping surface 158 on each flange 140 may engage a respective recess portion 151 on a respective leg 148 of the insulative member 114. This may provide a clamping force between the insulative member 114 and the rear wall 104 resulting in an insulative seal between the insulative member 114 and the rear wall 104. As another example, this may prevent the insulation member 114 from protruding into the internal chamber 102 so that the ventilation panel 110 (FIG. 3A) may be flush to the insulative member 114, or the rear wall 104, or both.

Figure 3:
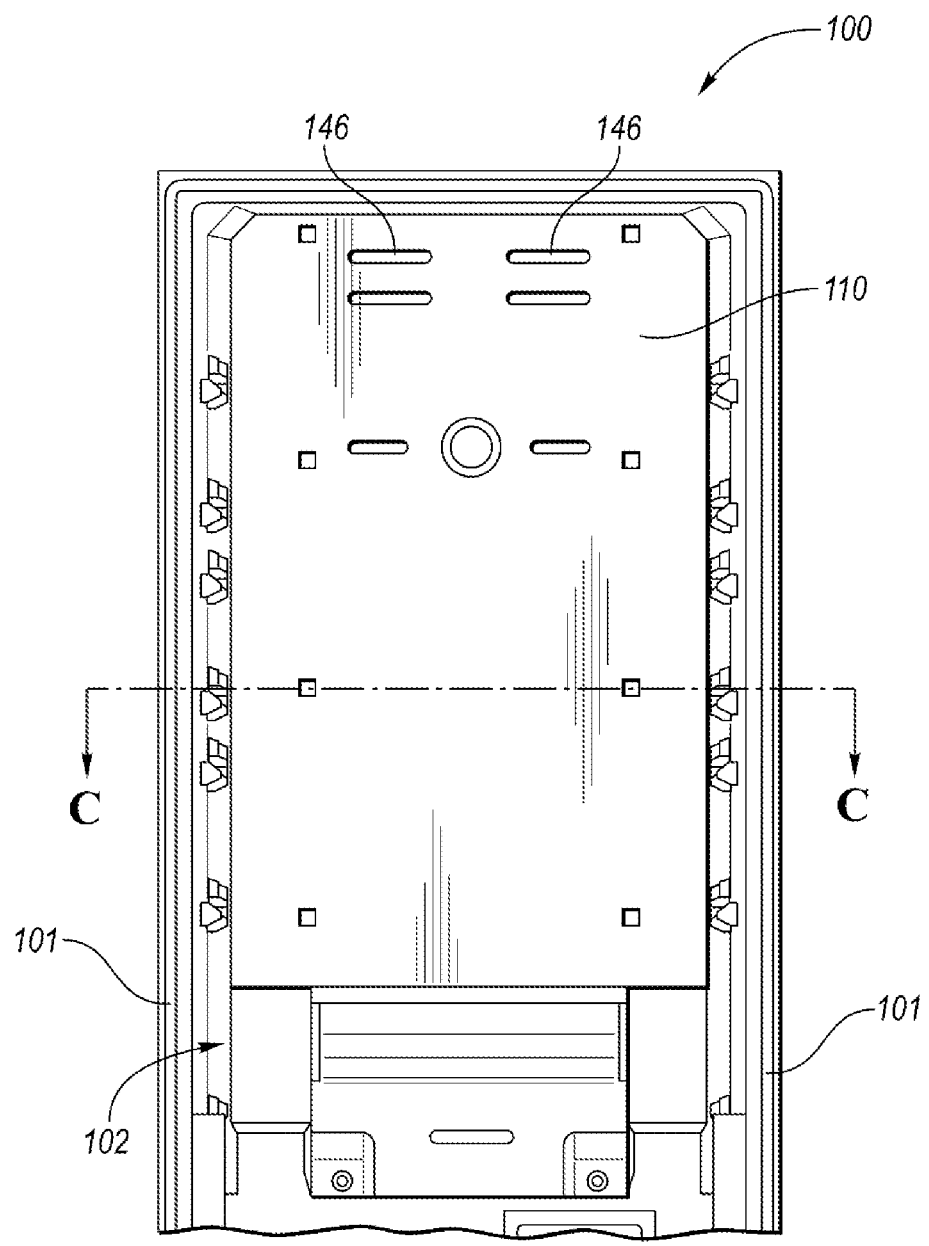
FIG. 3 illustrates a front view of a portion of the refrigerator including a vent panel with the shelving and storage bins removed.
Figure 3A:
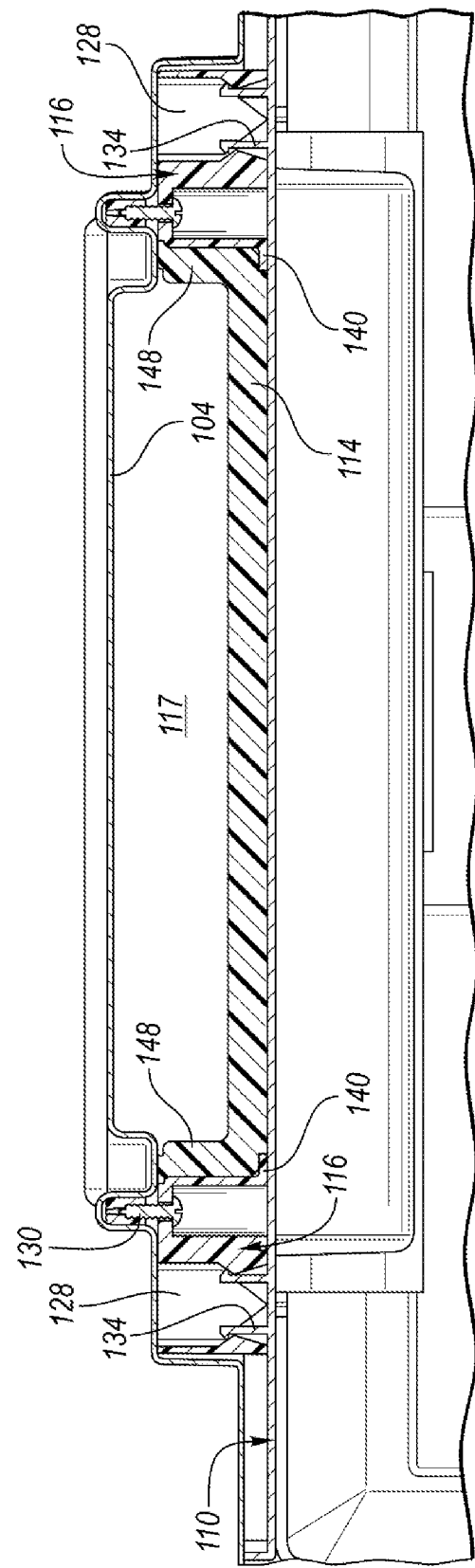
FIG. 3A is a cross-sectional view taken along line C-C in FIG. 3.
Figure 4:
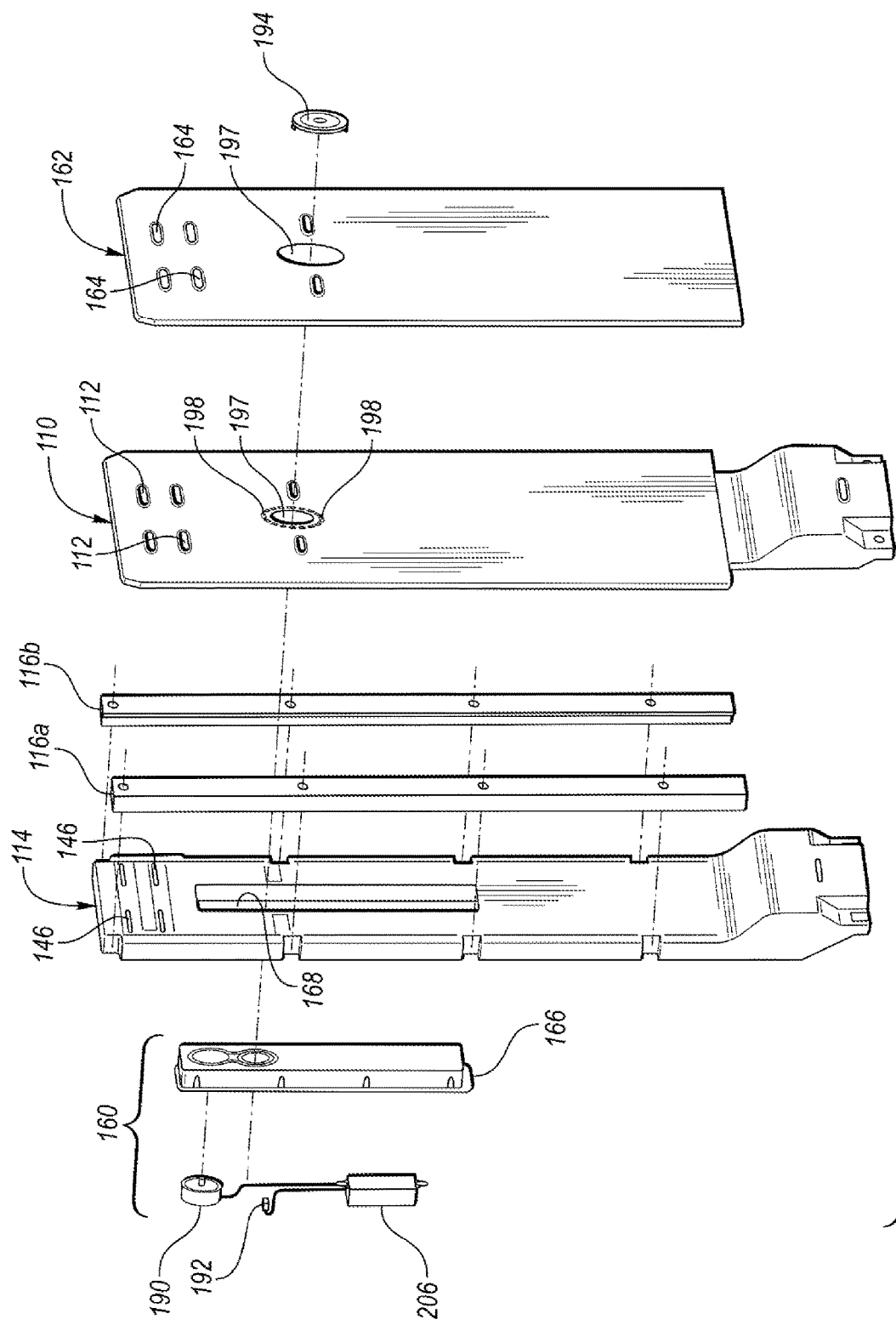
FIG. 4 is an exploded view of internal components of the refrigerator including an insulative member, a mounting system for the insulative member, and an ozone generator assembly.
Figure 7:
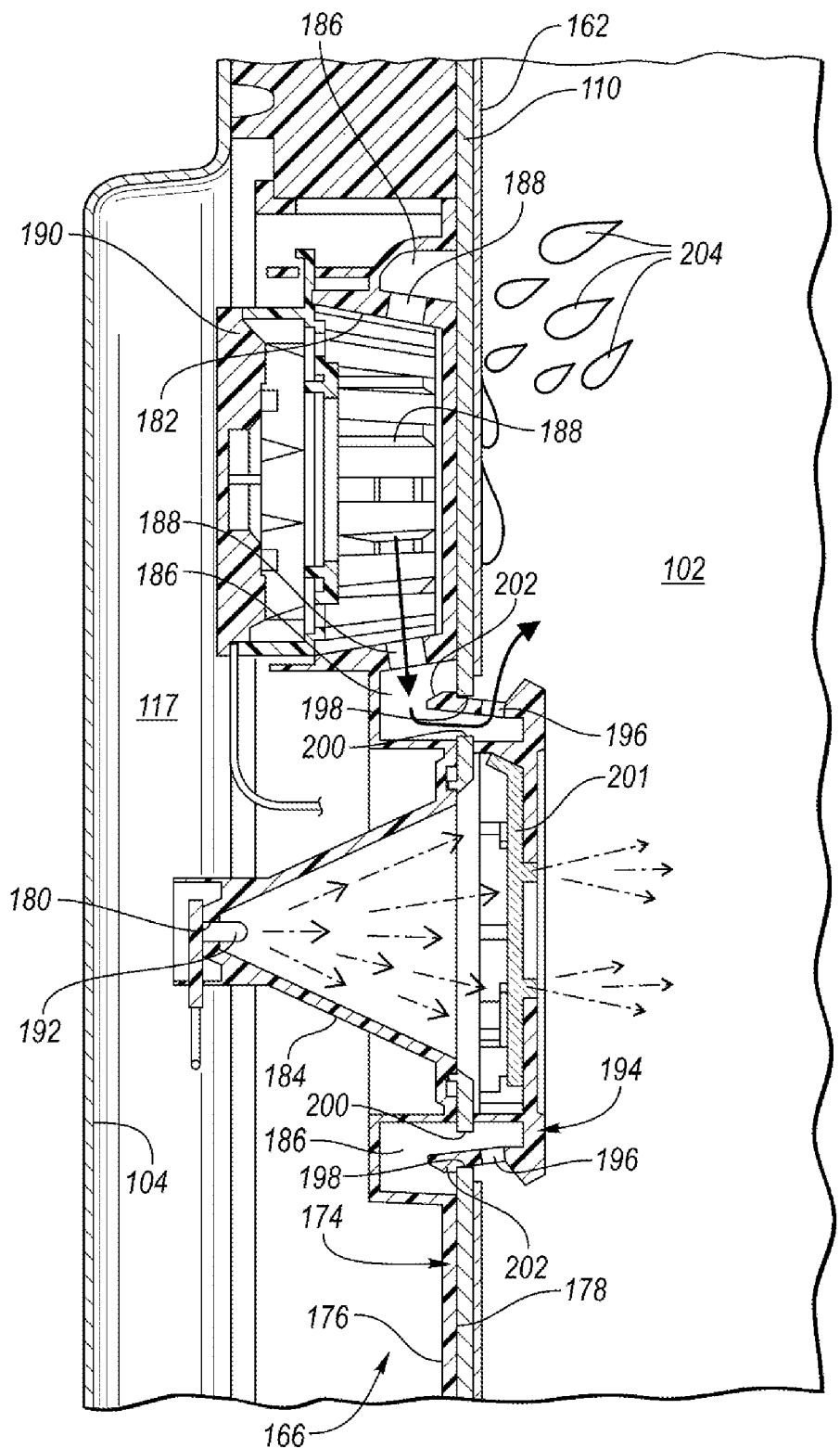
FIG. 7 is a partial cross-sectional view taken along line D-D in FIG. 1.

FIG. 3 illustrates a front view of a portion of the refrigerator 100 including the ventilation panel 110 with the shelving and storage bins removed. FIG. 3A illustrates a cross-sectional view taken along the line C-C in FIG. 3. The one or more second fasteners 134 are shown to protrude from the ventilation panel 110. However, it should be understood that the fasteners 134 may be components that are separate from the ventilation panel 110. Each of the one or more second fasteners 134 are also show to and to engage one of the one or more second apertures 128 to secure the ventilation panel 110 to the straps 116. Utilizing a press-fit fastener, such as the second one or more second fasteners 134, obviates excess assembly time required for a threaded fastener as well as the additional assembly time to insert a cover or plug to conceal the heads of threaded fasteners. The straps 116 and any associated feature or component (e.g., fasteners 130 and 134) may collectively be referred to as a fixation system for use in the refrigerator 100 that is configured to secure the insulative member 114 to the rear wall 104 and to secure the ventilation panel 110 to the insulative member 114.

Referring now to FIG. 4-9, some of the internal components of the refrigerator 100 including the insulative member 114, the mounting system for the insulative member (e.g., the fixation system that collectively includes the straps 116 and other components mentioned above), and an ozone generator assembly 160, are illustrated. The refrigerator 100 may also include a second ventilation or flow panel 162 that is disposed over the ventilation panel 110 to provide an aesthetic look. For example, the second ventilation panel 162 may be made from a finished metallic material such as aluminum or stainless steel. One or more apertures may form vents 164 in the second ventilation panel 162. The vents 164 in the second ventilation panel 162 may be substantially aligned with the vents 112 in the ventilation panel 110 and the vents 146 in the insulative member 114 such that the aligned vents may vent air from the internal chamber 102 to the exterior of the refrigerator 100 via the duct 117.

The ozone generator assembly 160 includes a housing 166. The insulative member 114 may define an aperture 168. The housing 166 may be disposed within the aperture 168. The housing 166 may include a top end 170, a bottom end 172, and a wall 174 extending between the top end 170 and the bottom end 172. The wall 174 includes an interior-facing surface 176 and an exterior-facing surface 178 that is opposite the interior-facing surface 176. The interior-facing surface 176 faces toward the duct 117. The exterior-facing surface 178 faces toward the internal chamber 102 of refrigerator 100. The ventilation panel 110 and the second ventilation panel 162 may be sandwiched between exterior-facing surface 178 of the wall 174 of the housing 166 and the internal chamber 102 of refrigerator 100. The exterior-facing surface 178 may be referred to as a frontside of the wall 174 and the interior-facing surface 176 may be referred to as a backside of the wall 174.

The wall 174 (or more specifically the interior-facing surface 176 of the wall 174) defines an aperture 180 and a pocket or receptacle 182 that is disposed above the aperture 180. The aperture 180 may be configured to receive a light source and may be defined within a recessed portion of the wall 174 that forms a light fixture 184. The exterior-facing surface 178 may have a recessed portion that extends inward from the exterior-facing surface 178 defining a trough 186. The recessed portion that extends inward from the exterior-facing surface 178 and/or the trough 186 may define the receptacle 182 on the interior-facing surface 176. The trough 186 may extend circumferentially about at least a portion of the receptacle 182 and about at least a portion of the light fixture 184. The housing 166 defines a first number of vents 188 that establish fluid communication between the receptacle 182 and the trough 186.

An ozone generator 190 is at least partially disposed in the receptacle 182. The ozone generator 190 is configured to supply ozonated fluid to the trough 186 via the receptacle 182 and the first number of vents 188. The ozonated fluid may be utilized to sanitize the internal chamber 102 of the refrigerator 100 or anything disposed within the internal chamber 102 of the refrigerator 100. A light 192 is secured to the wall 174 of housing 166. More specifically, the light 192 is secured to the light fixture 184 within the aperture 180. The light 192 and the light fixture 184 may be disposed between the bottom end 172 of the housing 166 and the ozone generator 190 (i.e., 192 the light fixture 184 may be disposed below the ozone generator 190). The light 192 may be a sanitizing light that is also utilized to sanitize the internal chamber 102 of the refrigerator 100 or anything disposed within the internal chamber 102 of the refrigerator 100. The light 192 may be any type of light including a light emitting diode (LED).

The light 192 may include a cover 194 that is disposed over the exterior-facing surface 178 (or more specifically, the light fixture 184) of the wall 174 of the housing 166. The cover 194 overlaps at least a portion of the trough 186. The cover 194 may define a second number of vents 196 that are configured to receive the ozonated fluid from the first number of vents 188 via the trough 186. The second number of vents 196 may be defined circumferentially around a radial outer surface of the cover 194. The second number of vents 196 may then provide the ozonated fluid to an interior portion (i.e., the internal chamber 102) of the refrigerator 100. The ventilation panel 110 and the second ventilation panel 162 may each define aligned apertures 197 that are disposed between the cover 194 and the light fixture 184 to allow light to travel from the light fixture 184 via the light 192 to the cover 194. The cover may include a front plate 199 and rear plate 201. The front plate may define an orifice 203 that is in the shape of symbol that is indicative of ozonated fluid. The rear plate 201 may be translucent and may be configured to direct the light from the light 192 to the orifice 203.

The ventilation panel 110 and the second ventilation panel 162 may be disposed over the trough 186 and at least a portion of the exterior-facing surface 178 of the wall 174. The ventilation panel 110 defines at least one slot 198. The slots of the at least one slot 198 may be disposed circumferentially about the aligned aperture 197 defined by the ventilation panel 110. The aligned aperture 197 defined by the second ventilation panel 162 may larger than the aligned aperture 197 defined by the ventilation panel 110 such that the aligned aperture 197 defined by the second ventilation panel 162 overlaps both the aligned aperture 197 defined by the ventilation panel 110 and the slots of the at least one slot 198. The at least one slot 198 may alternatively be referred to as at least one aperture or a plurality of apertures. The at least one slot 198 is in fluid communication with and is aligned with the trough 186. More specifically, an inner periphery 200 of the at least one slot 198 is in fluid communication with and is aligned with the trough 186. The at least one slot 198 is configured to receive ozonated fluid from the ozone generator 190 via the trough 186, first number of vents 188, and receptacle 182. The second number of vents 196 are in fluid communication with the at least one slot 198 and are configured to vent the ozonated fluid from the at least one slot 198 to an interior portion (i.e., the internal chamber 102) of the refrigerator 100.

The ozonated fluid is routed through a channel that collectively includes the receptacle 182, the first number of vents 188, the trough 186, the at least one slot 198, and the second number of vents 196. The cover 194 for the light 192 may include protrusions or legs 202 that extend into the slots of the at least one slot 198. The legs 202 may engage the ventilation panel 110 proximate the slots of the at least one slot 198 to secure the position of the cover 194. One or more of the legs 202 may define at least one of the second number of vents 196. This collective channel that includes the receptacle 182, the first number of vents 188, the trough 186, the at least one slot 198, and the second number of vents 196 routes the ozonated fluid downward from the ozone generator 190. The ozone generator 190, the receptacle 182, the first number of vents 188, and at least a portion of the trough 186 are then covered by the ventilation panel 110 (i.e., the ventilation panel 110 overlays the exterior-facing surface 178 of the wall 174). Routing the ozonated fluid downward and covering the ozone generator 190, the receptacle 182, the first number of vents 188, and at least a portion of the trough 186 prevents an ingress of fluid 204, such as water, into the ozone generator 190, which could result in damage to the ozone generator 190.

The ozone generator 190 and the light 192 may each be connected to an electrical box or electrical block 206 via wires 208. The electrical block 206 may include a controller or may be connected to a controller that is configured to operate the ozone generator 190 and the light 192. The controller may be configured to, responsive to receiving first signals from the ozone generator 190 that are indicative of a first operating condition, provide second signals to the light 192 to display an indicator, wherein the indicator is configured to communicate the first operating condition to a user. The operating condition may at least partially be based on a quantity of ozonated fluid being supplied to the internal chamber 102 of the refrigerator 100 via the channel that collectively includes the receptacle 182, the first number of vents 188, the trough 186, the at least one slot 198, and the second number of vents 196.

More specifically, the controller may be configured to receive signals from the ozone generator 190 that is indicative of the ozone generator 190 being off, the ozone generator 190 being on, or a quantity of ozonated fluid being supplied to the internal chamber 102 of the refrigerator 100, each being a different operating condition. The controller may then send signal to the light 192 to illuminate the light 192, to turn off the light 192, dim the light 192, brighten the light, or strobe the light 192 to correspond to a specific operating condition. For example, the light 192 being off may correspond to the ozone generator 190 being off, the light 192 being on may correspond to the ozone generator 190 being on, an increase in the brightness of the light 192 may correspond to an increase in the quantity of ozonated fluid being supplied to the internal chamber 102, a decrease in the brightness of the light 192 may correspond to a decrease in the quantity of ozonated fluid being supplied to the internal chamber 102, etc.

The controller may be part of a larger control system and may be controlled by various other controllers throughout the refrigerator 100. It should therefore be understood that the controller and one or more other controllers can collectively be referred to as a "controller" that controls various functions or components of the refrigerator 100 in response to signals from various sensors to control the various functions or components of the refrigerator. The controller may include a microprocessor or central processing unit (CPU) in communication with various types of computer readable storage devices or media. Computer readable storage devices or media may include volatile and nonvolatile storage in read-only memory (ROM), random-access memory (RAM), and keep-alive memory (KAM), for example. KAM is a persistent or non-volatile memory that may be used to store various operating variables while the CPU is powered down. Computer-readable storage devices or media may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller in controlling the refrigerator 100.

It should be understood that the designations of first, second, third, fourth, etc. for any component, state, or condition described herein may be rearranged in the claims so that they are in chronological order with respect to the claims.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A fixation system for use in a refrigerator comprising:
   an insulative member;
   a ventilation panel defining a number of vents;
   a first strap; and
   a second strap spaced apart from the first strap, wherein the first strap and the second strap are collectively configured to receive the insulative member, wherein the first and second straps engage (i) first and second side edges of the insulative member, respectively, and (ii) a front surface of the insulative member to secure the insulative member to a rear wall of the refrigerator, wherein the first strap includes a main body having a rear side and a front side opposing the rear side, wherein the rear side lies against the rear wall of the refrigerator and defines a first aperture configured to receive a first fastener to fix the main body to the rear wall of the refrigerator, wherein the front side defines a second aperture receiving a second fastener to fix the ventilation panel to the main body, wherein the second fastener is a press-fit fastener extending from the ventilation panel, wherein the second aperture is configured to receive the press-fit fastener, wherein the second aperture (i) extends axially inward from the front side of the main body, (ii) is tapered radially inward along a first region that is (a) adjacent to the front side of the main body and (b) operable to guide the press-fit fastener into the second aperture, and (iii) is tapered radially outward along a second region that extends from the first region such that a protrusion is defined along a transition between the first region and the second region, and wherein the press-fit fastener engages the protrusion to within the second aperture to secure the ventilation panel to the second strap.

2. The fixation system of claim 1, wherein first strap includes (i) a sidewall extending between the rear side and the front side and (ii) a flange extending laterally outward therefrom, wherein the sidewall engages the first side edge of the insulative member, wherein the flange engages the front surface of the insulative member, and wherein the flange is disposed between the insulative member and the ventilation panel.

3. The fixation system of claim 2, wherein the first aperture is spaced apart from the sidewall by a first width and the second aperture is spaced apart from the sidewall by a second width, wherein the second width is greater than the first such that the second aperture is spaced apart from and does not overlap the first aperture.

4. The fixation system of claim 2, wherein the front surface of the insulative member defines a recessed region, and wherein the flange engages the front surface of the insulative member within the recessed region.

5. The fixation system of claim 1, wherein the first aperture is a counterbore hole and the first strap includes a clamping surface configured to engage the insulative member as the first fastener is tightened such that a portion of the insulative member is compressed as the fixation system is fixed to the rear wall of the refrigerator.

6. The fixation system of claim 1, wherein the second strap includes a second main body having a second rear side and a second front side opposing the second rear side, wherein the second rear side lies against the rear wall of the refrigerator and defines a third aperture configured to receive a third fastener to fix the second main body to the rear wall of the refrigerator, wherein the second front side defines a fourth aperture receiving a fourth fastener to fix the ventilation panel to the second main body, wherein second strap includes (i) a second sidewall extending between the second rear side and the second front side and (ii) a second flange extending laterally outward therefrom, wherein the second sidewall engages the second side edge of the insulative member, wherein the second flange engages the front surface of the insulative member, and wherein the second flange disposed between the insulative member and the ventilation panel.

7. The fixation system of claim 1, wherein the insulative member has a length extending between a top and a bottom of the insulative member, and wherein the first and second straps extend between the top and bottom of the insulative member along at least half of the length.

8. A refrigerator subcomponent fixation system comprising:
   a rear wall;
   an insulative member;
   a first strap and a second strap (i) each fixed to the rear wall, (ii) engaging first and second opposing side edges of the insulative member, respectively, and (iii) each engaging a front surface of the insulative member to secure the insulative member to the rear wall, wherein (a) the first and second straps include sidewalls and flanges extending laterally outward from the sidewalls, (b) the sidewalls of the first and second straps engage the first and second opposing side edges of the insulative member, respectively, (c) the flanges engage the front surface of insulative member to secure the insulative member to the rear wall, (d) the first and second straps define counterbore orifices adjacent to the flanges, (e) the counterbore orifices are configured to receive fasteners to fix the first and second straps to the rear wall, (f) the first and second straps define a second set of orifices that are spaced apart from the counterbore orifices, (g) the orifices of the second set of orifices (I) extend axially inward from front sides of the first and second straps, (II) and are tapered radially inward along first regions that are (A) adjacent to the front sides of the first and second straps and (B) operable to guide press-fit fasteners into the second set of orifices, and (III) are tapered radially outward along second regions that extend from the first regions such that protrusions are defined along transitions between the first regions and the second regions; and
   a ventilation panel secured to the first and second straps such that the insulative member is sandwiched between the rear wall and the ventilation panel, and wherein the press-fit fasteners extend from the ventilation panel and engage the protrusions within the second set of orifices to secure the ventilation panel to the first and second straps.

9. The refrigerator subcomponent fixation system of claim 8, wherein the insulative member has a length extending between a top and a bottom of the insulative member, and wherein the first and second straps extend between the top and bottom the insulative member along at least half of the length.

10. The refrigerator subcomponent fixation system of claim 8, wherein the front surface of the insulative member defines recessed regions, and wherein the flanges engage the front surface of the insulative member within the recessed regions.

11. A refrigerator subcomponent mounting system comprising:
   a rear wall;
   a ventilation panel spaced apart from the rear wall;
   an insulative member disposed between the rear wall and the ventilation panel, the insulative member having opposing side edges and a front surface extending between the opposing side edges;
   first and second straps (i) disposed between the rear wall and the ventilation panel, (ii) fixed to the rear wall, (iii) engaging the opposing side edges and the front surface of the insulative member to secure the insulative member to the rear wall, and (iv) defining orifices; and
   press-fit fasteners extending from the ventilation panel, wherein the orifices (i) are tapered radially inward along first regions that are operable to guide the press-fit fasteners into the orifices and (ii) tapered radially outward along second regions that extend from the first regions such that protrusions are defined along transitions between the first regions and the second regions within each orifice, and wherein each press-fit fastener engages the protrusion within one of the orifices to secure the ventilation panel to the first and second straps.

12. The refrigerator subcomponent mounting system of claim 11, wherein the first and second straps include sidewalls and flanges extending laterally outward from the sidewalls, and wherein the sidewalls engage the opposing side edges of the insulative member and the flanges engage the front surface of the insulative member to secure the insulative member to the rear wall.

13. The refrigerator subcomponent mounting system of claim 12, wherein the front surface of the insulative member defines recessed regions, and wherein the flanges engage the front surface of the insulative member within the recessed regions.

14. The refrigerator subcomponent mounting system of claim 11, wherein the insulative member has a length extending between a top and a bottom of the insulative member, and wherein the first and second straps extend between the top and bottom the insulative member along at least half of the length.

* * * * *